(12) United States Patent
Fiedler

(10) Patent No.: US 10,350,142 B1
(45) Date of Patent: Jul. 16, 2019

(54) PROGRAMMABLE MEDICINE DISPENSER

(71) Applicant: Patricia Fiedler, Glenside, PA (US)

(72) Inventor: Patricia Fiedler, Glenside, PA (US)

(*) Notice: Subject to any disclaimer, the term of this patent is extended or adjusted under 35 U.S.C. 154(b) by 288 days.

(21) Appl. No.: 15/484,237

(22) Filed: Apr. 11, 2017

(51) Int. Cl.
*A61J 7/04* (2006.01)
*A61J 7/00* (2006.01)
*G07F 11/44* (2006.01)
*G06F 19/00* (2018.01)

(52) U.S. Cl.
CPC ........... *A61J 7/0418* (2015.05); *A61J 7/0076* (2013.01); *A61J 7/0436* (2015.05); *G06F 19/3462* (2013.01); *G07F 11/44* (2013.01); *A61J 2200/30* (2013.01)

(58) Field of Classification Search
CPC ...... A61J 7/0418; A61J 7/0076; A61J 7/0436; A61J 2200/30; G07F 11/44; G06F 19/3462
USPC ................................................. 700/231–244
See application file for complete search history.

(56) References Cited

U.S. PATENT DOCUMENTS

| 7,359,765 B2* | 4/2008 | Varvarelis | A61J 7/0481 |
| | | | 700/237 |
| D604,835 S | 11/2009 | Conley | |
| 7,896,192 B2 | 3/2011 | Conley | |
| 9,014,847 B2 | 4/2015 | Dunn | |
| 9,245,093 B2 | 1/2016 | Shaw | |
| 2009/0223994 A1 | 9/2009 | Getz | |
| 2012/0130534 A1* | 5/2012 | Wurm | G06Q 20/203 |
| | | | 700/236 |
| 2016/0022543 A1 | 1/2016 | Deeter | |
| 2017/0000692 A1* | 1/2017 | Mullen | A61J 7/0076 |

FOREIGN PATENT DOCUMENTS

WO 2008079426 7/2008

* cited by examiner

*Primary Examiner* — Michael Collins
(74) *Attorney, Agent, or Firm* — Kyle A. Fletcher, Esq.

(57) ABSTRACT

The programmable medicine dispenser is a secured pill dispenser. The programmable medicine dispenser is a locked dispenser that: 1) dispenses a controlled medical substance at the single dose level; and 2) controls access to the contents of the locked dispenser. The programmable medicine dispenser: 1) dispenses the controlled medical substance in single dose quantities; 2) dispenses a single dose of the controlled medical substance at regular intervals; 3) verifies the physical presence of a patient before releasing the single dose of the controlled medical substance; 4) notifies the appropriate authority that a single dose has been dispensed; 5) limits access to the hopper of programmable medicine dispenser to a pharmacy or other secured location; and, 6) operates a beacon to locate the programmable medicine dispenser. The programmable medicine dispenser comprises a dispenser and a control system. The control system is stored within and controls access to the dispenser.

17 Claims, 8 Drawing Sheets

| Line Number | Figure Ref # | Action |
|---|---|---|
| 1 | 151 | Decision1: Received Message From Appropriate Authority (172)? |
| 2 | | Yes: Go to Line 4 |
| 3 | | No: Go to Line 9 |
| 4 | 161 | Action 1: Update Overide and Reset Timers as Directed |
| 5 | 162 | Action 2: Update Dose as Directed |
| 6 | 163 | Action 3: Send GPS Coordinates Message as Directed |
| 7 | 164 | Action 4: Open Hopper (112) as Directed |
| 8 | 165 | Action 5: Lock Hopper (112) as Directed |
| 9 | 152 | Decision 2: Time to Release Next Door |
| 10 | | Yes: Go to Line 12 |
| 11 | | No: Go to Line 1 |
| 12 | 166 | Action 6: Release Next Door |
| 13 | 167 | Action 7: Restart Timer |
| 14 | 168 | Action 8: Send Message to Appropriate Authority (172) that Dose is Released |
| 15 | | Go to Line 1 |

FIG. 7

PROGRAMMABLE MEDICINE DISPENSER

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical and veterinary science including a container adapted for medical and pharmaceutical purposes, more specifically, a programmed container with time indication for taking medication.

SUMMARY OF INVENTION

The programmable medicine dispenser is a secured pill dispenser that is configured for use with controlled medical substances. The programmable medicine dispenser is a locked dispenser that: 1) dispenses the controlled medical substance at the single dose level; and 2) controls access to the contents of the locked dispenser. The specific security protocols implemented by the programmable medicine dispenser include: 1) dispensing the controlled medical substance in single dose quantities; 2) dispensing a single dose of the controlled medical substance at regular intervals previously determined by an appropriate authority; 3) verifying the physical presence of a patient before releasing the single dose of the controlled medical substance; 4) notifying the appropriate authority that a single dose has been dispensed; 5) limiting access to the hopper of programmable medicine dispenser to a pharmacy or other secured location; and, 6) operation of a beacon capability to locate the programmable medicine dispenser should the programmable medicine dispenser be lost or stolen.

These together with additional objects, features and advantages of the programmable medicine dispenser will be readily apparent to those of ordinary skill in the art upon reading the following detailed description of the presently preferred, but nonetheless illustrative, embodiments when taken in conjunction with the accompanying drawings.

In this respect, before explaining the current embodiments of the programmable medicine dispenser in detail, it is to be understood that the programmable medicine dispenser is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the programmable medicine dispenser.

It is therefore important that the claims be regarded as including such equivalent construction insofar as they do not depart from the spirit and scope of the programmable medicine dispenser. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

FIG. 7 is a flowchart of an embodiment of the disclosure.

DETAILED DESCRIPTION OF THE EMBODIMENT

Figure 1:
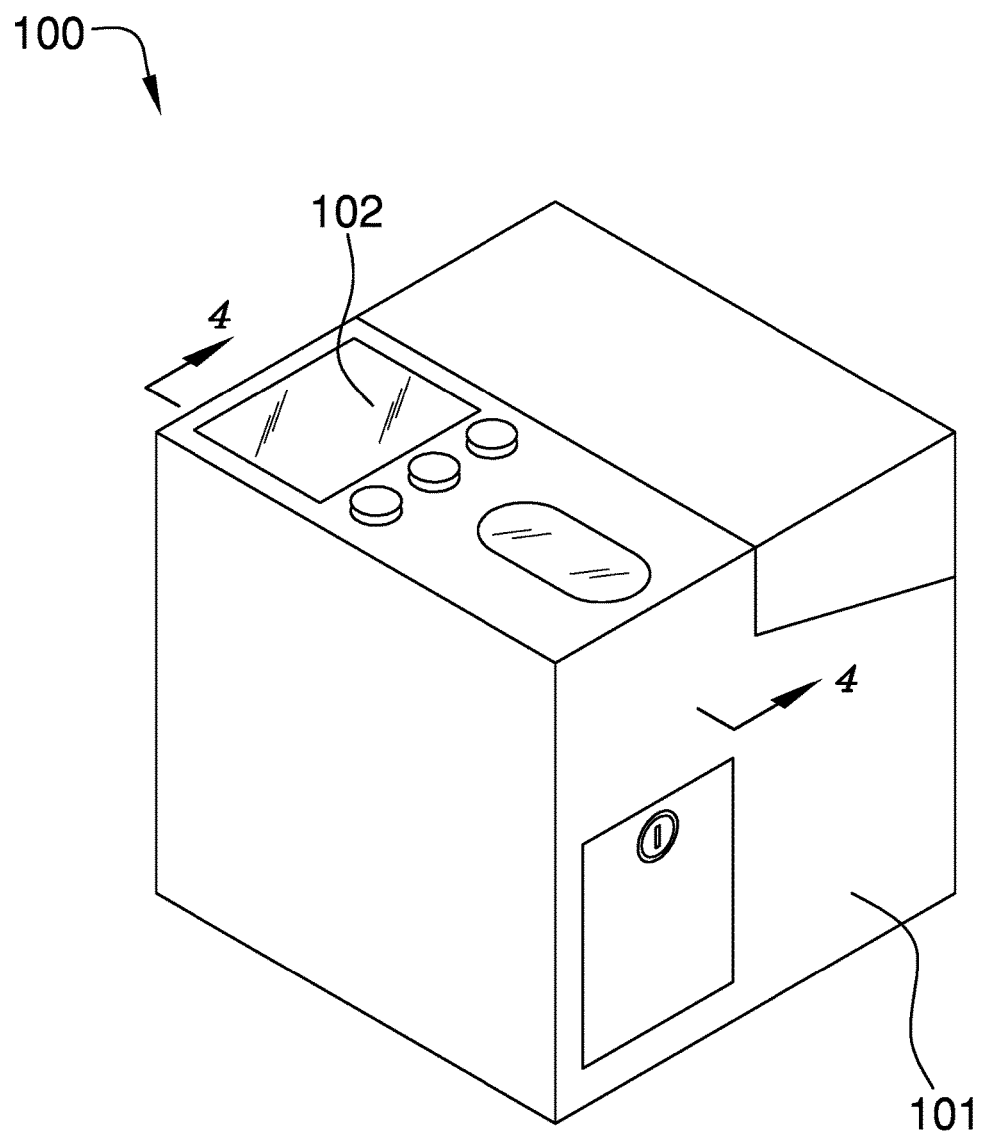
FIG. 1 is a perspective secured view of an embodiment of the disclosure.
Figure 2:
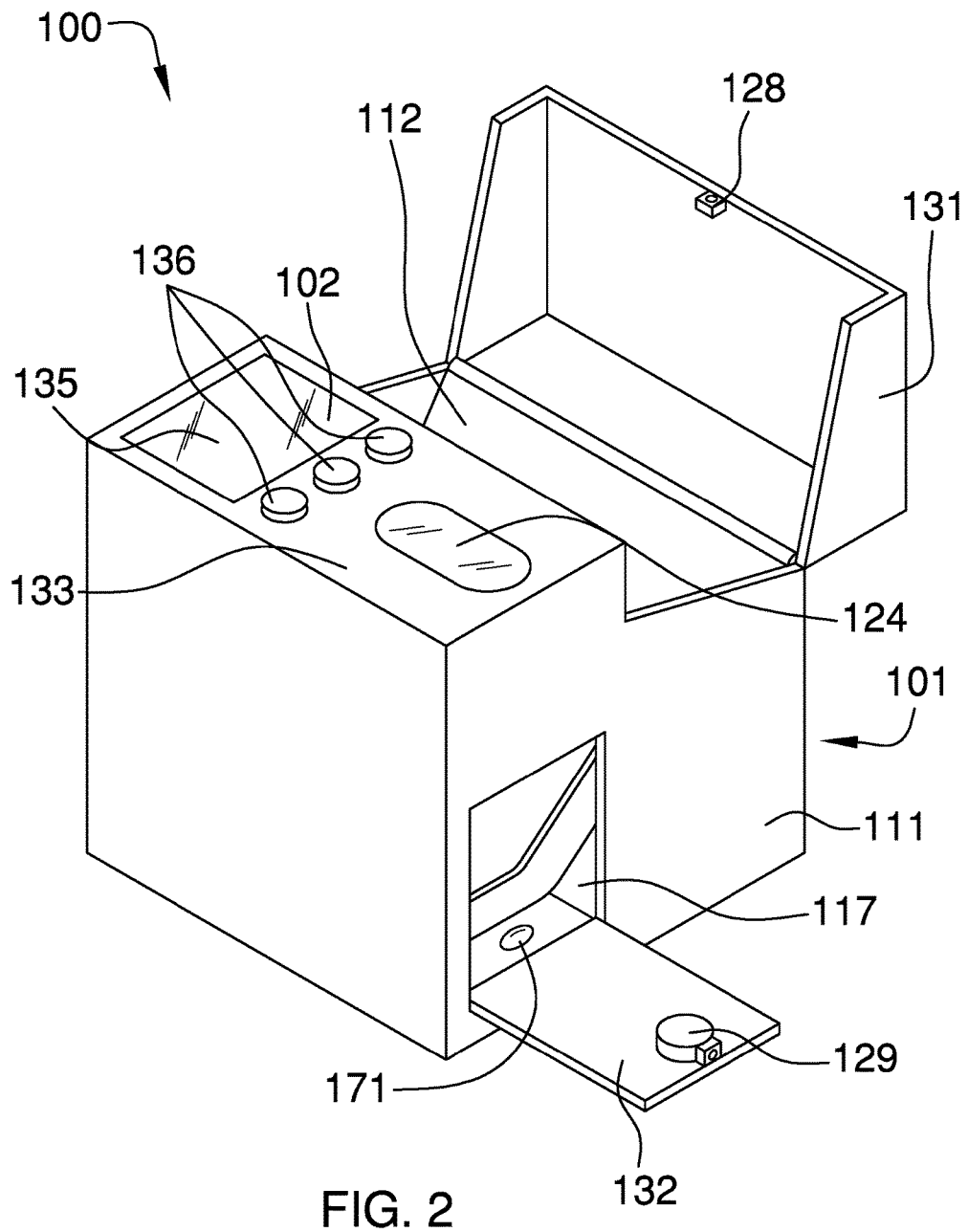
FIG. 2 is a perspective unsecured view of an embodiment of the disclosure.
Figure 3:
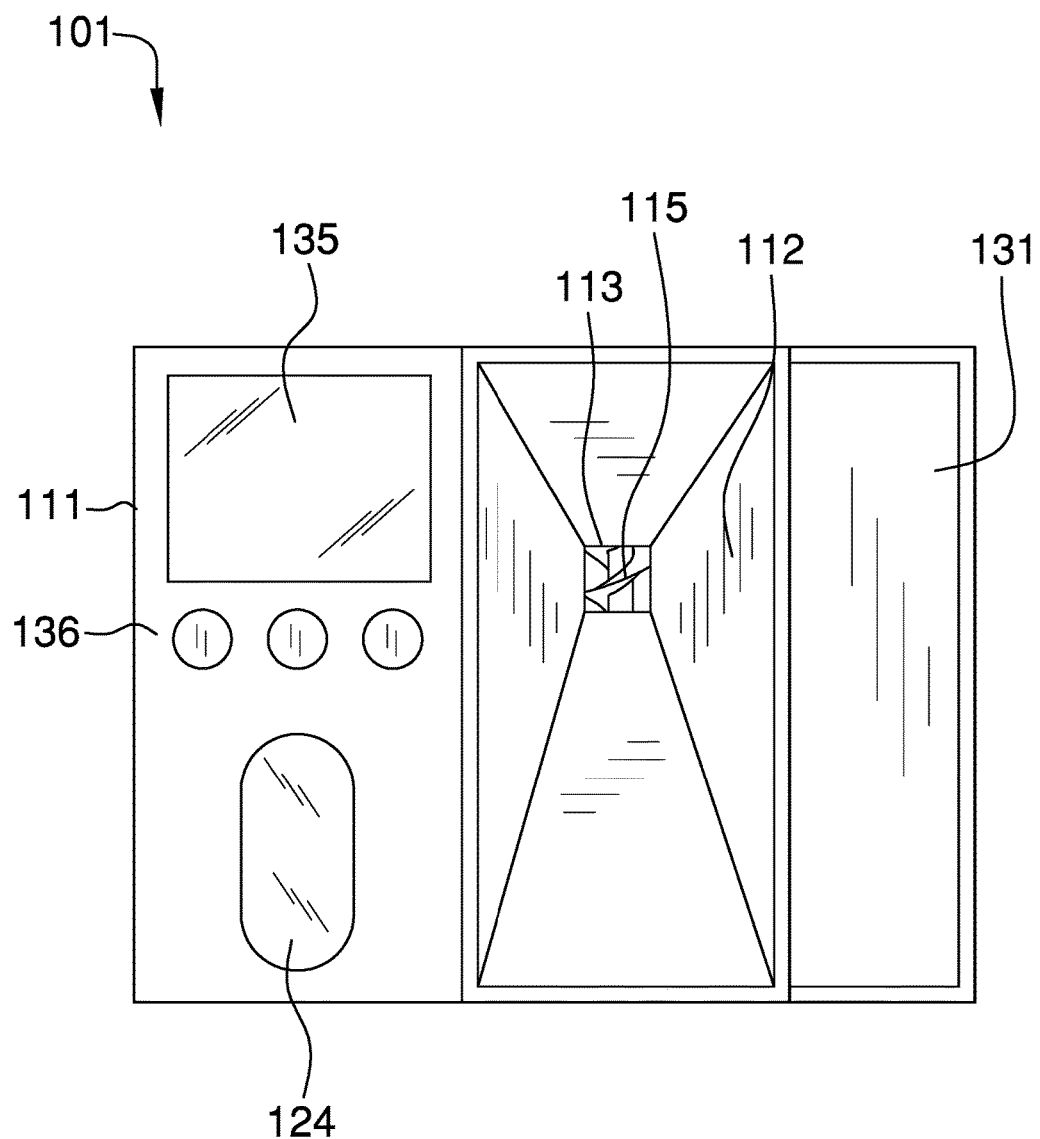
FIG. 3 is a top unsecured view of an embodiment of the disclosure.

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to one or more potential embodiments of the disclosure, which are illustrated in FIGS. 1 through 8.

The programmable medicine dispenser 100 (hereinafter invention) is a secured pill dispenser 101 that is configured for use with a controlled medical substance 171. The controlled medical substance 171 refers to a drug that has a high potential for misuse by a patient 173. The patient 173 refers to a person who is taking the controlled medical substance 171. The invention 100 is a locked dispenser 101 that: 1) dispenses the controlled medical substance 171 at the single dose level; and 2) controls access to the contents of the locked dispenser 101. The specific security protocols implemented by the invention 100 include: 1) dispensing the controlled medical substance 171 in single dose quantities; 2) dispensing a single dose of the controlled medical substance 171 at regular intervals previously determined by an appropriate authority 172; 3) verifying the physical presence of a patient 173 before releasing the single dose of the controlled medical substance 171; 4) notifying the appropriate authority 172 that a single dose has been dispensed; 5) limiting access to the hopper 112 of the dispenser 101 to a pharmacy or other secured location; and, 6) operation of a beacon capability to locate the invention 100 should the invention 100 be lost or stolen. The invention 100 comprises a dispenser 101 and a control system 102. The control system 102 is stored within and controls access to the dispenser 101.

Within the context of this disclosure, it is assumed that the appropriate authority 172 refers to a physician who is: 1) prescribing the controlled medical substance 171 to the patient 173; and, 2) sending operational instructions over SMS to the control system 102. Based on the organizational structure of the health care system, this responsibility may be delegated to other persons or organizations.

The dispenser 101 is a secured container within which the plurality of doses of the controlled medical substance 171 are stored and from which the single dose of the controlled medical substance 171 is dispensed. The dispenser 101 physically houses the control system 102. The dispenser 101 is an access controlled structure. It is preferred that the dispenser 101 be formed from a metal such as steel. The dispenser 101 comprises a housing 111, a hopper 112, an auger port 113, an auger channel 114, an auger 115, a dispensing port 116, and a dispensing chamber 117.

The housing 111 is a metal casing within which the control system 102 and the controlled medical substance 171 are contained. The housing 111 is formed with all necessary apertures and form factors required to allow the housing 111 to accommodate the intended use and operation of the invention 100.

The hopper 112 is a storage cavity that is formed within the dispenser 101. The hopper 112 stores a plurality of doses of the controlled medical substance 171 form which the control system 102 dispenses single doses of the controlled medical substance 171. Access to the hopper 112 is controlled by the appropriate authority 172 such that access to the hopper 112 is limited to periods when the dispenser 101 is under the physical control of a pharmacy. When the dispenser 101 is in the physical control of a pharmacy, the appropriate authority 172 will send a message to the control system 102 instructing the control system 102 to release the first lock 128 thereby providing the pharmacy access to the hopper 112.

Figure 4:
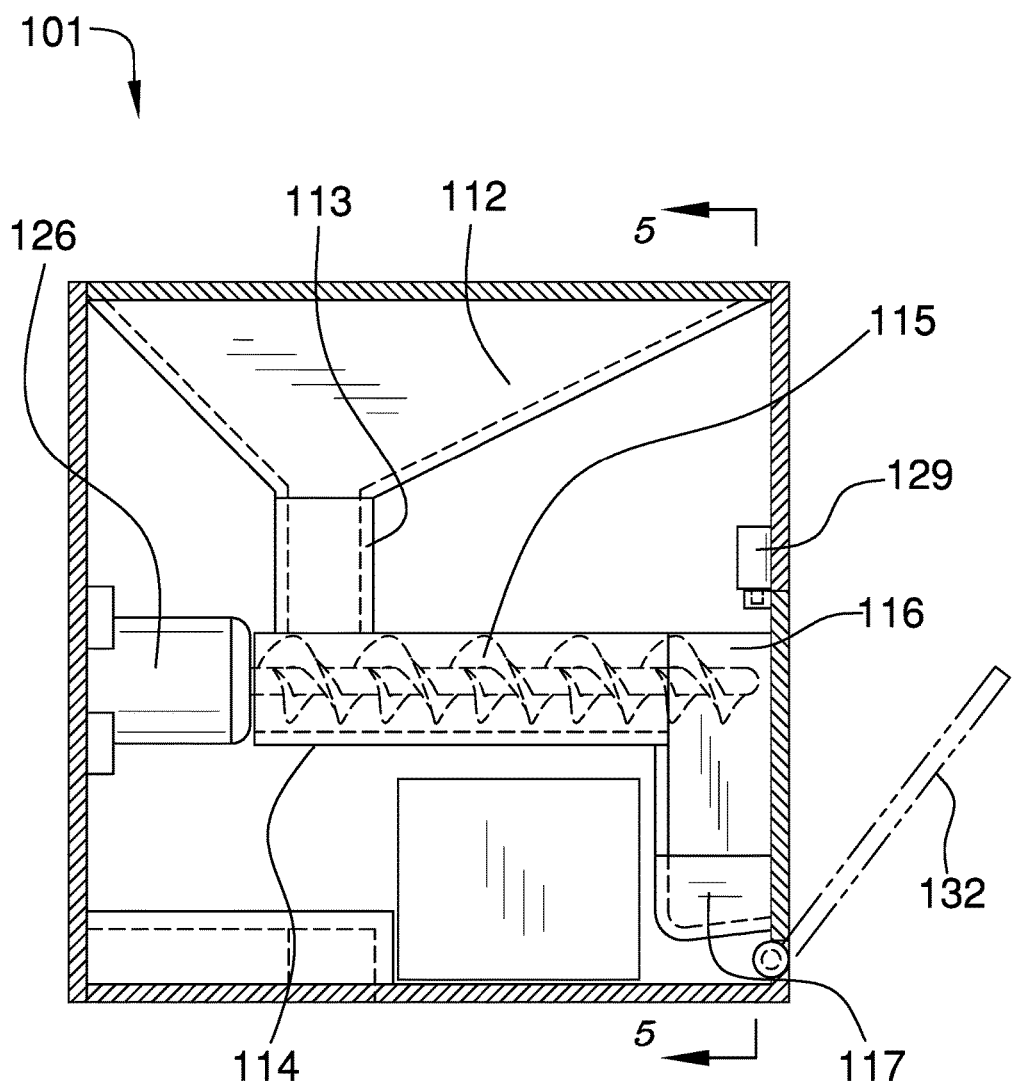
FIG. 4 is a cross-sectional view of an embodiment of the disclosure across 4-4 as shown in FIG. 1.

As shown most clearly in FIG. 4, the auger port 113 is a gravity feed tube that attaches the hopper 112 to the auger channel 114 such that the controlled medical substance 171 will fall from the hopper 112 into the auger channel 114. The auger channel 114 is a tube within which the auger 115 is contained. The auger 115 is a mechanical device that is formed with an exterior screw thread such that the rotation of the auger 115 will move one or more doses of the controlled medical substance 171 from the hopper 112 to the dispensing port 116. The use of an auger 115 for this purpose is well known and documented in the mechanical arts.

Figure 5:
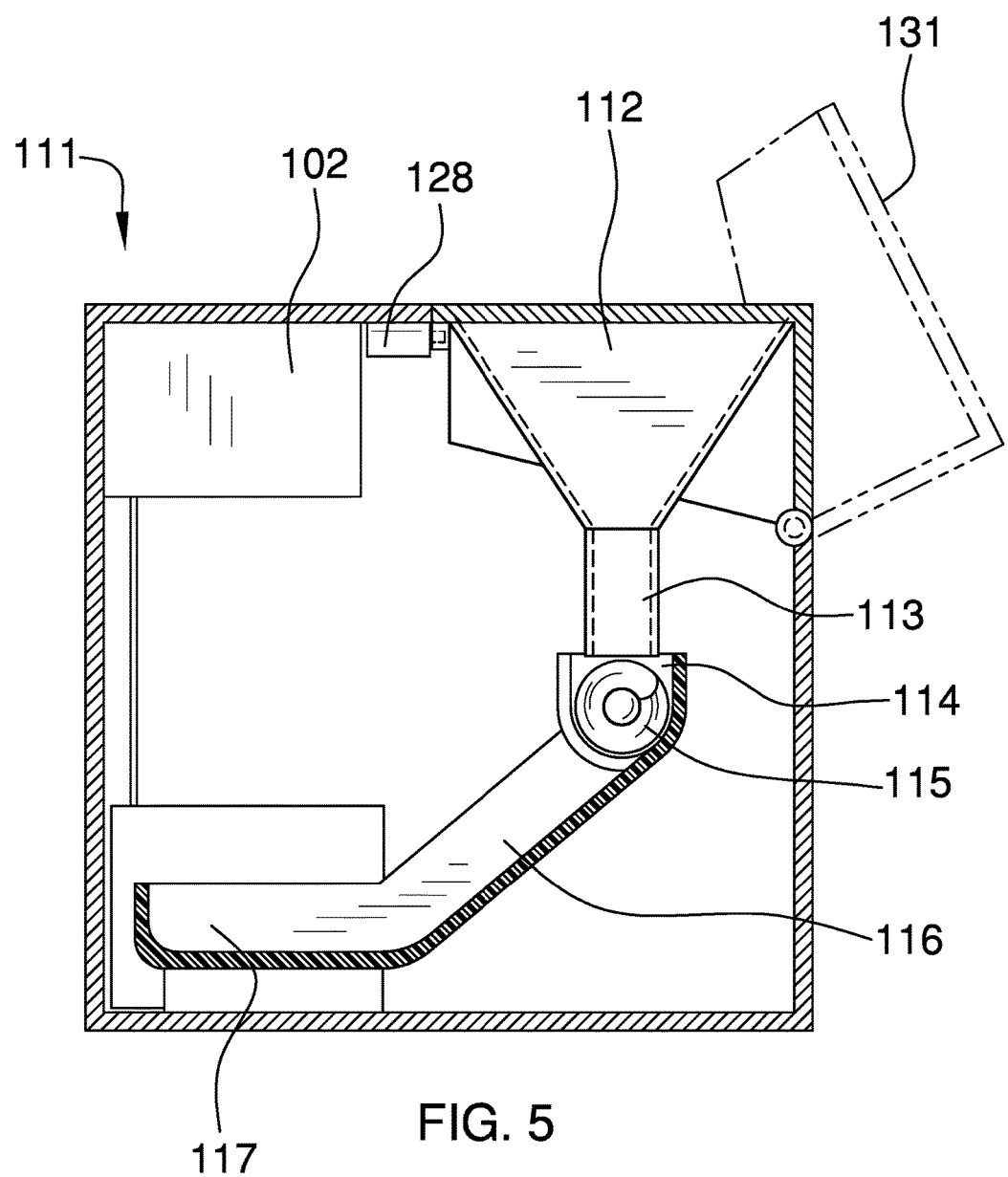
FIG. 5 is a cross-sectional view of an embodiment of the disclosure across 5-5 as shown in FIG. 4.
Figure 6:
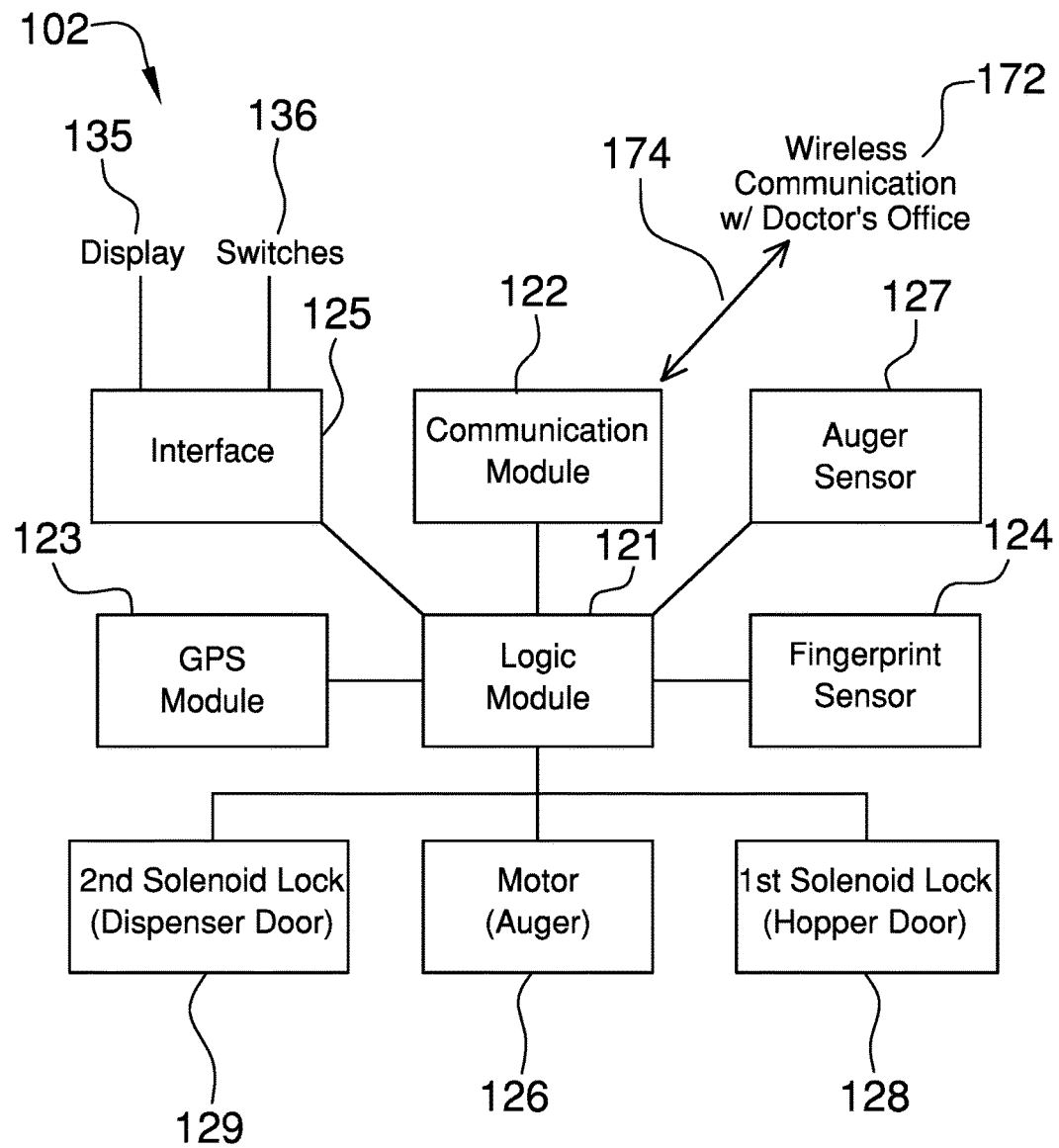
FIG. 6 is a block diagram of an embodiment of the disclosure.
Figure 8:
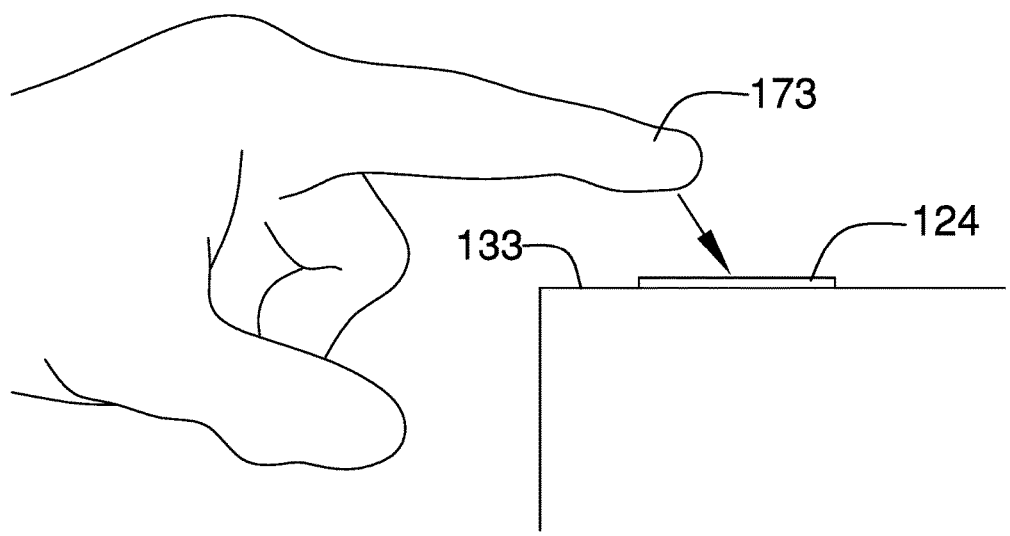
FIG. 8 is a detail view of an embodiment of the disclosure.

As shown most clearly in FIG. 5, the dispensing port 116 is a trough that receives a single dose of the controlled medical substance 171 from the auger 115 and transports the single dose of the controlled medical substance 171 to the dispensing chamber 117. The dispensing chamber 117 is a storage cavity that is formed within the dispenser 101. The dispensing chamber 117 holds the single dose of the controlled medical substance 171 until the single dose is released.

The housing 111 further comprises a hopper door 131, a dispensing door 132, and a display plate 133. The hopper door 131 is a hinged door that is used to control external access into the hopper 112. The dispensing door 132 is a hinged door that is used to control external access into the dispensing chamber 117. The display plate 133 is a faceplate through which the display 135, the plurality of switches 136, and the fingerprint sensor 124 are mounted in a manner accessible from the exterior of the housing 111.

The control system 102 is an electronic device that: 1) controls access to the controlled medical substance 171 contained within the dispenser 101; 2) receives programming and instructions directly from an appropriate authority 172; 3) receives programming and instructions remotely from the appropriate authority 172, and, 4) verifies the identity and presence of the patient 173 before dispensing a single dose of the controlled medical substance 171. Access to the operation of the control system 102 by the patient 173 is limited to releasing a single dose of the controlled medical substance 171 from the dispenser 101 for immediate consumption. Otherwise, the control system 102 is managed and regulated remotely by the appropriate authority 172.

The control system 102 releases the single dose of the controlled medical substance 171 after the identity of the patient 173 has been confirmed. Upon release of the single dose of the controlled medical substance 171, the control system 102 sends a message to the appropriate authority 172 informing the appropriate authority 172 that the single dose of the controlled medical substance 171 has been dispensed.

The control system 102 comprises a logic module 121, a communication module 122, a GPS module 123, a fingerprint sensor 124, a local interface 125, an auger motor 126, an auger sensor 127, a first lock 128, and a second lock 129.

The logic module 121 is a readily and commercially available programmable electronic device that is used to manage, regulate, and operate the control system 102. Depending on the specific design and the selected components, the logic module 121 can be a separate component within the control system 102 or the functions of the logic module 121 can be incorporated into another component within the control system 102.

The communication module 122 is a readily and commercially available wireless electronic communication device that allows the logic module 121 to communicate over a commercially provided and publicly available cellular wireless network 174. The commercially provided and publicly available cellular wireless network 174 is a commercial service that provides wireless voice and messaging services to personal data devices such as cellular phones.

In the first potential embodiment of the disclosure, the communication module 122 communicates SMS and MMS messages between the logic module 121 and the appropriate authority 172 through a commercially provided and publicly available cellular wireless network 174. The use of a commercially provided and publicly available cellular wireless network 174 is preferred because: 1) of its low cost; 2) of its widespread availability and broad interoperability between competing commercially provided and publicly available cellular wireless networks 174; and, 3) methods and techniques to send SMS and MMS messages over a commercially provided and publicly available cellular wireless network 174 are well known and documented by those skilled in the electrical arts.

The GPS module 123 is an electrical device that communicates with the GPS to determine the GPS coordinates of the GPS module 123. When queried by the logic module 121, the GPS module 123 transfers the GPS coordinates to the logic module 121.

The fingerprint sensor 124 is a commercially available electrical security device. The fingerprint sensor 124 is a sensor that scans the fingerprint of the patient 173 and codes the scan into an electrical signal. In the first potential embodiment of the disclosure an ADH-Tech GT-511C3 fingerprint scanner is used as the fingerprint sensor 124. The GT-511C3 is an "all-in-one" device that: 1) registers the fingerprint of the patient 173; 2) stores the registered fingerprint of the patient 173; 3) scans a fingerprint during the process of releasing a single dose of the controlled medical substance 171; 4) compares the scanned fingerprint to the registered fingerprint of the patient 173; and, 5) upon a fingerprint match sends a signal to the logic module 121 verifying the fingerprint match.

The local interface 125 is a user interface that is provides a limited operational interface between the control system 102 and the patient 173 for the purpose of releasing a single dose of the controlled medical substance 171. The local interface 125 further comprises a display 135 and a plurality of switches 136. The display 135 is a readily and commercially available LCD display 135 that displays text based messages to the patient 173. Each of the plurality of switches 136 is a readily and commercially available electric switch that are used to allow a patient 173 to input operational decisions to the logic module 121.

The auger motor 126 is a commercially available electric motor. The auger motor 126 is used to rotate the auger 115 for the purpose of transporting a single dose of the controlled medical substance 171 from the auger port 113 to the dispensing port 116. The operation of the auger motor 126 is controlled by the logic module 121.

The auger sensor 127 is a break beam sensor that is mounted at the point where the auger channel 114 attaches to the dispensing port 116. The auger sensor 127 is monitored by the logic module 121. As a single dose of the controlled medical substance 171 passes into the dispensing port 116, the single dose breaks the beam of the break beam sensor. This interruption is detected by the logic module 121, which then discontinues the operation of the auger motor 126.

The first lock 128 is a first electrically controlled lock that is commonly referred to as a solenoid lock. The first lock 128 is controlled by the logic module 121. The first lock 128 is used to secure the hopper door 131 of the hopper 112. The second lock 129 is a second electrically controlled lock that is commonly referred to as a solenoid lock. The second lock 129 is controlled by the logic module 121. The second lock 129 is used to secure the dispensing door 132 of the dispensing chamber 117.

As shown most clearly in FIG. 7, the operation of the control system 102 is described in the following 3 paragraphs.

The logic module 121 makes a first decision 151 as to whether a message has been received from the appropriate authority 172 by checking the communication module 122. If no message has been received from the appropriate authority 172, the logic module 121 proceeds to the second decision 152. If a message has been received from the appropriate authority 172, the logic module 121 takes a first action 161 of overriding, updating and resetting any timers being used to determine dosage intervals when so directed through the message from the appropriate authority 172. The logic module 121 next takes a second action 162 of updating, when so directed through the message from the appropriate authority 172, the dosage of the controlled medical substance 171 that is to be dispensed. The logic module 121 next takes a third action 163, when so directed through the message from the appropriate authority 172, of querying the GPS module 123 for the GPS coordinates of the GPS module 123 and forwarding the GPS coordinates to the appropriate authority 172 through the communication module 122.

The logic module 121 next takes a fourth action 164, when so directed by the appropriate authority 172, of releasing the first lock 128 to provide access to the hopper 112. After the hopper 112 is filled, the logic module 121 next takes a fifth action 165, when so directed by the appropriate authority 172, of locking the first lock 128 to secure to the hopper 112.

The logic module 121 makes a second decision 152 as to whether enough time has elapsed to release the next single dose of the controlled medical substance 171. The logic module 121 maintains and tracks this schedule through the use of internal timers commonly available in a commercially available logic module 121. If the scheduled time for the next single dose has not elapsed the logic module 121 will loop back to the first decision 151. If the scheduled time for the next single dose has elapsed, the logic module 121 takes a sixth action 166 of releasing the second lock 129 to provide access to the dispensing chamber 117. The logic module 121 will release the second lock 129 once the fingerprint sensor 124 has verified that the patient 173 is physically present at the invention 100. The logic module takes a seventh action 167 or resetting the dosage timers. The logic module 121 takes an eighth action 168 of sending a message through the communication module 122 to the appropriate authority 172 indicating that the single dose of the controlled medical substance 171 has been dispensed. The logic module 121 then loops back to the first decision 151.

Appropriate Authority: As used in this disclosure, an appropriate authority is a previously determined person or organization that is designated to receive alarm or other notification messages regarding a monitored system or activity.

Auger: As used in this disclosure, an auger is a cylinder or a cone that is formed with an exterior screw thread. One purpose of an auger is to use the rotation of the auger to move an object through a linear distance through a pipe.

Break Beam Sensor: As used in this disclosure, a break beam sensor is a motion sensing device. The break beam sensor comprises a beam generator and a beam detector. The beam generator generates a beam of electromagnetic radiation (visible or not visible) that detected by the beam detector. The beam of electromagnetic radiation forms a trip wire in the sense that if an object passes through the transmission of the beam of electromagnetic radiation is interrupted. This interruption of the beam of electromagnetic radiation is detected via the beam detector. The interruption of the beam of electromagnetic radiation is taken to imply that an object has moved through area within which the beam of electromagnetic radiation is transmitted.

Cavity: As used in this disclosure, a cavity is an empty space that is formed within an object.

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; 4) the point, pivot, or axis around which something revolves; or, 5) the centroid or first moment of an area or structure. In cases where the appropriate definition or definitions are not obvious, the fifth option should be used in interpreting the specification.

Center Axis: As used in this disclosure, the center axis is the axis of a cylinder or cone like structure. When the center axes of two cylinder or like structures share the same line they are said to be aligned. When the center axes of two cylinder like structures do not share the same line they are said to be offset.

Control System: As used in this disclosure, a control system is a first device or system that manages and regulates the behavior or operation of a second device or system.

Cylinder: As used in this disclosure, a cylinder is a geometric structure defined by two identical flat and parallel ends, also commonly referred to as bases, which are circular in shape and connected with a single curved surface, referred to in this disclosure as the face. The cross section of the cylinder remains the same from one end to another. The axis of the cylinder is formed by the straight line that connects the center of each of the two identical flat and parallel ends of the cylinder. Unless otherwise stated within this disclosure, the term cylinder specifically means a right cylinder which is defined as a cylinder wherein the curved surface perpendicularly intersects with the two identical flat and parallel ends.

Display: As used in this disclosure, a display is a surface upon which is presented an image, potentially including, but not limited to, graphic images and text, that is interpretable by an individual viewing the projected image in a meaningful manner.

Electric Motor: In this disclosure, an electric motor is a machine that converts electric energy into rotational mechanical energy.

Exterior: As used in this disclosure, the exterior is use as a relational term that implies that an object is not contained within the boundary of a structure or a space.

Exterior Screw Thread: An exterior screw thread is a ridge wrapped around the outer surface of a tube in the form of a helical structure that is used to convert rotational movement into linear movement.

Form Factor: As used in this disclosure, the term form factor refers to the size and shape of an object.

GPS: As used in this disclosure, depending on the context GPS refers to: 1) a system of navigational satellites that are used to determine the position and velocity of a person or object; 2) the system of navigational satellites referred to in the first definition that are used to synchronize to global time; or, 3) an electronic device or that uses the system of navigational satellites referred to in the first definition to determine the position of a person or object. GPS is an acronym for Global Positioning System.

Housing: As used in this disclosure, a housing is a rigid casing that encloses and protects one or more devices.

Interior: As used in this disclosure, the interior is use as a relational term that implies that an object is contained within the boundary of a structure or a space.

LCD: As used in this disclosure, LCD is an acronym for Liquid Crystal Display. A liquid crystal display comprises a liquid crystal film placed between two sheets of transparent material. The visual characteristics of the can be varied through the application of a voltage.

Logic Module: As used in this disclosure, a logic module is a readily and commercially available electrical device that is programmable and that accepts digital and analog inputs, processes the digital and analog inputs according to previously stored instruction and provides the results of these instructions as digital or analog outputs.

Motor: As used in this disclosure, a motor refers to the method of transferring energy from an external power source into mechanical energy.

Personal Data Device: As used in this disclosure, a personal data device is a handheld device that is used for managing personal information and communication. Examples of personal data device include, but are not limited to, cellular phones, tablets and smart phones.

Sensor: As used in this disclosure, a sensor is a device that receives and responds in a predetermined way to a signal or stimulus. As further used in this disclosure, a threshold sensor is a sensor that generates a signal that indicates whether the signal or stimulus is above or below a given threshold for the signal or stimulus.

SMS: As used in this disclosure, SMS is an abbreviation for short message service. The short message service is a service that is often provided with the cellular services that support personal data devices. Specifically, the SMS allows for the exchange of written messages between personal data devices. The SMS is commonly referred to as text messaging. A common enhancement of SMS is the inclusion of the delivery of multimedia services. This enhanced service is often referred to as Multimedia Media Services which is abbreviated as MMS.

Solenoid: As used in this disclosure, a solenoid is a cylindrical coil of electrical wire that generates a magnetic field that can be used to mechanically move a shaft made of a magnetic core.

Switch: As used in this disclosure, a switch is an electrical device that starts and stops the flow of electricity through an electric circuit by completing or interrupting an electric circuit. The act of completing or breaking the electrical circuit is called actuation. Completing or interrupting an electric circuit with a switch is often referred to as closing or opening a switch respectively. Completing or interrupting an electric circuit is also often referred to as making or breaking the circuit respectively.

Timing Circuit: As used in this disclosure, a timing circuit refers to an electrical network of interconnected electrical elements, potentially including but not limited to, resistors, capacitors, diodes, transistors, and integrated circuit devices. The purpose of the timing circuit is to generate an electrical control signal after a predetermined amount of time. In common usage, a timing circuit is also referred to as timing circuitry.

Timing Device: As used in this disclosure, a timing device is an automatic mechanism for activating or deactivating a device at a specific time.

Trough: As used in this disclosure, a trough is an open receptacle that is used to: 1) store a fluid in a manner accessible to an animal; or, 2) to physically determine and limit the flow path of a fluid. The rain gutter commonly seen on a building is an example of a trough.

With respect to the above description, it is to be realized that the optimum dimensional relationship for the various components of the invention described above and in FIGS. 1 through 8 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A programmed container comprising:
    wherein the programmed container comprises a dispenser and a control system;
    wherein the control system is stored within the dispenser;
    wherein the programmed container is configured for use with a controlled medical substance;
    wherein the programmed container is adapted for use with a patient;
    wherein the dispenser is a locked dispenser;
    wherein the control system controls access to the contents of the dispenser;
    wherein the programmed container is remotely operated by an authority;
    wherein programmed container dispenses the controlled medical substance in single dose quantities;
    wherein programmed container dispenses a single dose of the controlled medical substance at regular intervals previously determined by an authority;
    wherein programmed container verified the physical presence of a patient before releasing the single dose of the controlled medical substance;
    wherein programmed container notifies the authority that a single dose has been dispensed;
    wherein programmed container limits access to the stores of the controlled medical substance to a pharmacy or other secured location;
    wherein programmed container operates a beacon capable of locating the programmed container;
    wherein the control system comprises a logic module, a communication module, a GPS module, a fingerprint sensor, an auger motor, an auger sensor, a first lock, and a second lock;
    wherein the communication module, the GPS module, the fingerprint sensor, the local interface, the auger motor, the auger sensor, the first lock, and the second lock are electrically connected to the logic module;
    wherein the fingerprint sensor is a commercially available security device;
    wherein the fingerprint sensor is a sensor that scans the fingerprint of the patient;
    wherein the fingerprint sensor codes the scan of a registered patient into an electrical signal;
    wherein the fingerprint sensor stores the registered fingerprint of the patient;
    wherein the fingerprint sensor scans a fingerprint during the process of releasing a single dose of the controlled medical substance;
    wherein the fingerprint sensor compares the scanned fingerprint to the registered fingerprint of the patient;
    wherein the fingerprint sensor sends a signal to the logic module verifying the fingerprint match.

2. The programmed container according to claim 1
    wherein the dispenser comprises a housing, a hopper, an auger port, an auger channel, an auger, a dispensing port, and a dispensing chamber;
    wherein the hopper, the auger port, the auger channel, the auger, the dispensing port, and the dispensing chamber are contained within the dispenser.

3. The programmed container according to claim 2
    wherein the housing is a casing within which the control system and the controlled medical substance are contained.

4. The programmed container according to claim 3
    wherein the hopper is a storage cavity that is formed within the dispenser;
    wherein access to the hopper is controlled by the authority such that access to the hopper is limited to periods when the dispenser is under the physical control of a pharmacy.

5. The programmed container according to claim 4
    wherein the auger port is a gravity feed tube that attaches the hopper to the auger channel such that the controlled medical substance will fall from the hopper into the auger channel;
    wherein the auger channel is a tube within which the auger is contained;
    wherein the auger is a mechanical device that is formed with an exterior screw thread.

6. The programmed container according to claim 5 wherein the dispensing port is a trough that receives a single dose of the controlled medical substance from the auger and transports the single dose of the controlled medical substance to the dispensing chamber.

7. The programmed container according to claim 6 wherein the dispensing chamber is a storage cavity that is formed within the dispenser.

8. The programmed container according to claim 7
    wherein the housing further comprises a hopper door and a dispensing door;
    wherein the hopper door is a hinged door that controls external access into the hopper;
    wherein the dispensing door is a hinged door that is used to control external access into the dispensing chamber.

9. The programmed container according to claim 8
    wherein the control system is an electronic device;
    wherein the control system controls access to the controlled medical substance contained within the dispenser;
    wherein the control system receives programming and instructions directly from the authority;
    wherein the control system receives programming and instructions remotely from the authority;
    wherein the control system verifies the identity and presence of the patient before dispensing a single dose of the controlled medical substance.

10. The programmed container according to claim 9 wherein the communication module is wireless electronic communication device that allows the logic module to communicate over a commercially provided and publicly available cellular wireless network.

11. The programmed container according to claim 10
    wherein the GPS module is an electrical device that communicates with the GPS to determine the GPS coordinates of the GPS module;
    wherein the GPS module transfers the GPS coordinates to the logic module.

12. The programmed container according to claim 11
    wherein the auger motor is an electric motor;
    wherein the auger motor rotates the auger;
    wherein the operation of the auger motor is controlled by the logic module.

13. The programmed container according to claim 12
    wherein the auger sensor is a break beam sensor;
    wherein the auger sensor is mounted at the point where the auger channel attaches to the dispensing port;
    wherein the auger sensor is monitored by the logic module.

14. The programmed container according to claim 13
    wherein the first lock is a first electrically controlled lock that is referred to as a solenoid lock;
    wherein the first lock is controlled by the logic module;

wherein the first lock is used to secure the hopper door of the hopper.

15. The programmed container according to claim 14 wherein the second lock is a second electrically controlled lock that is referred to as a solenoid lock;

wherein the second lock is controlled by the logic module;

wherein the second lock is used to secure the dispensing door of the dispensing chamber.

16. The programmed container according to claim 15 wherein the logic module is a programmable electronic device.

17. The programmed container according to claim 15 wherein the logic module is a programmable electronic device;

wherein the logic module makes a first decision as to whether a message has been received from the authority;

wherein the logic module takes a first action of overriding, updating and resetting any timers being used to determine dosage intervals;

wherein the logic module next takes a second action of updating the dosage of the controlled medical substance that is to be dispensed;

wherein the logic module next takes a third action of querying the GPS module for the GPS coordinates of the GPS module and forwarding the GPS coordinates to the authority;

wherein the logic module next takes a fourth action of releasing the first lock to provide access to the hopper;

wherein the logic module next takes a fifth action of locking the first lock to secure to the hopper;

wherein the logic module makes a second decision as to whether enough time has elapsed to release the next single dose of the controlled medical substance;

wherein the logic module takes a sixth action of releasing the second lock to provide access to the dispensing chamber;

wherein the logic module releases the second lock after the fingerprint sensor has verified that the registered fingerprint of the patient;

wherein the logic module will then send a message through the communication module to the authority indicating that the single dose of the controlled medical substance has been dispensed;

wherein the logic module takes a seventh action or resetting the dosage timers;

wherein the logic module takes an eighth action of send a message through the communication module to the authority indicating that the single dose of the controlled medical substance has been dispensed.

* * * * *